(12) United States Patent
Yamamoto et al.

(10) Patent No.: US 8,772,529 B2
(45) Date of Patent: Jul. 8, 2014

(54) CATALYST FOR ALKYLATION AND PROCESS FOR PRODUCING ALKYLAROMATIC HYDROCARBON COMPOUND USING THE CATALYST

(75) Inventors: Yasushi Yamamoto, Yamaguchi (JP); Hikaru Yatabe, Yamaguchi (JP)

(73) Assignee: UBE Industries, Ltd, Yamaguchi (JP)

( * ) Notice: Subject to any disclaimer, the term of this patent is extended or adjusted under 35 U.S.C. 154(b) by 0 days.

(21) Appl. No.: 13/642,327

(22) PCT Filed: Jun. 3, 2011

(86) PCT No.: PCT/JP2011/062771
§ 371 (c)(1),
(2), (4) Date: Oct. 19, 2012

(87) PCT Pub. No.: WO2011/155400
PCT Pub. Date: Dec. 15, 2011

(65) Prior Publication Data
US 2013/0041174 A1    Feb. 14, 2013

(30) Foreign Application Priority Data
Jun. 10, 2010  (JP) ................. 2010-132708

(51) Int. Cl.
*C07C 67/00* (2006.01)
(52) U.S. Cl.
USPC .......................................... 560/96
(58) Field of Classification Search
USPC ...................... 560/96, 76; 502/100
See application file for complete search history.

(56) References Cited

U.S. PATENT DOCUMENTS

| 5,849,652 | A * | 12/1998 | Davies et al. ............ 502/60 |
| 2003/0147805 | A1 | 8/2003 | Koegler et al. |
| 2004/0162454 | A1 | 8/2004 | Gao et al. |

FOREIGN PATENT DOCUMENTS

| EP | 0769489 A1 * | 7/1996 |
| JP | 2-045429 | 2/1990 |
| JP | 8-020548 | 1/1996 |
| JP | 9-132552 | 5/1997 |
| JP | 2007-523075 | 8/2007 |
| JP | 2007-238490 | 9/2007 |
| WO | WO 2002/072519 A2 * | 9/2002 |

OTHER PUBLICATIONS

Thomas et al. (Rare earth exchanged (Ce3+, La3+ and RE3+) H-Y zeolites as solid acid catalysts for the synthesis of linear alkyl benzenes, Microporous and Mesoporous Materials, vol. 95, 329-338, (2006).*
White et al. (Basic Energy Sciences Advisory Committee Subpanel Workshop Report, Opportunities for Catalysis in the 21st Century, 2002, pp. 1-47).*
Mikami et al. teach (Asymetric Catalysis by Lanthanide Complexes, Angew. Chem. Int. Ed., vol. 41, 3554-3571, 2002) (pp. 3555-3556).*
Yoneda, Norihiko et al., Electrophilic Substitution of Benzenes With Strong Electron-Withdrawing Groups in Super Acid Media, Friedel-Crafts Alkylation of Acetophenone, Chemistry Letters, 1979, pp. 1003-1006, Chemical Society of Japan.
Kim, Jae Nyoung et al., Friedel-Crafts Cyclohexylation of Arenes with 1,3-Dicyclohexylcarbodiimide (DCC), Tetrahedron Letters, 1994, pp. 903-904, vol. 35, No. 6, Elsevier Science, Ltd., Great Britain.
International Search Report, PCT/JP2011/062771, Aug. 30, 2011.
Thomas, B. et al., Rare earth exchanged (Ce3+, La3+ and RE3+) H-Y zeolites as solid acid catalysts for the synthesis of linear alkyl benzenes, Microporous and Mesoporous Materials, Jul. 20, 2006, vol. 95, No. 1-3, p. 329-338, doi:10.1016/j.micromeso.2006.05.035.
Hoefnagel. A.J. et al., Selective Alkylation of Methylbenzenes with Cyclohexene Catalyzed by Solid Acids, Catalysis Letters, Jan. 2003, vol. 85, No. 1-2, p. 7-11, DOI:1023/A:1022152304209.

* cited by examiner

*Primary Examiner* — Brandon Fetterolf
*Assistant Examiner* — Blaine G Doletski
(74) *Attorney, Agent, or Firm* — Young & Thompson

(57) ABSTRACT

A catalyst for alkylation contains an inorganic structural material having an ion-exchange ability and a metal ion having a valency of 2 or more. The metal ion is supported on the inorganic structural material. The inorganic structural material is preferably a zeolite. The metal ion is preferably a lanthanide metal. The catalyst for alkylation imparts industrially satisfiable activity and selectivity and can be readily separated, collected and recycled. Furthermore, the process for producing an alkylaromatic hydrocarbon compound includes reacting an aromatic hydrocarbon compound and a compound having an unsaturated bond in the presence of the catalyst for alkylation.

3 Claims, No Drawings

CATALYST FOR ALKYLATION AND PROCESS FOR PRODUCING ALKYLAROMATIC HYDROCARBON COMPOUND USING THE CATALYST

TECHNICAL FIELD

The present invention relates to a catalyst for alkylation and a process for producing an alkylaromatic hydrocarbon compound using the catalyst.

BACKGROUND ART

Alkylation is an important reaction that is conducted very frequently in chemical industries. However, in the case when alkylation is conducted in an industrial scale, the problem of safeness and risk are significant. For example, reactions have been habitually conducted by using highly toxic chemical substances or at a high temperature in many cases, and in the case when these reactions are carried out in an industrial scale, they have the problem of high toxicity.

Examples of conventional alkylation include 1) a process using sulfuric acid or hydrogen fluoride as a catalyst (see Non-Patent Literature 1), and 2) a process using a catalyst containing aluminum chloride (see Non-Patent Literature 2). However, since either of these processes uses an acid or halogen-containing substance having high corrosiveness, a countermeasure for preventing corrosion of apparatuses and a post-treatment for separating and collecting the reacted catalyst are necessary, and thus the steps are complicated. Therefore, either of known processes was not suitable as an industrial process and was not sufficiently suitable.

In order to make easily the separation of a catalyst after a reaction, a solid catalyst that is readily separated and collected from a reaction liquid is preferable, but the activity thereof is not suitable. For example, it was reported that a Friedel-Crafts alkylation of toluene and cyclohexene was conducted by using a solid catalyst, but the reaction was performed by adding a solid catalyst containing an inorganic structural material showing an acidic property such as a zeolite and a clay in an amount equal to or more than the amount of the cyclohexene as a raw material (see Non-Patent Literature 3). It is difficult for carrying out in an industrial scale to use 100% or more by mass of a solid catalyst with respect to raw materials.

CITATION LIST

Non-Patent Literatures

Non-Patent Literature 1: Chem Lett., 1003 (1979)
Non-Patent Literature 2: Tetrahedron Lett., 35, 903 (1994)
Non-Patent Literature 3: Catalysis Letters, 85, 7 (2003)

SUMMARY OF INVENTION

Technical Problem

In view of the above-mentioned current situation, the problem of the present invention is to provide a catalyst for alkylation which imparts industrially suitable activity and selectivity and can be readily separated, collected and recycled, and a process for producing an alkylaromatic hydrocarbon compound using that catalyst.

Solution to Problem

The present inventors have done intensive studies so as to solve the above-mentioned problem, and found that a catalyst for alkylation which expresses industrially suitable activity and selectivity is formed by supporting a specific metal on a specific inorganic structural material. Furthermore, they have also found that, since this catalyst is a solid catalyst, it can be readily separated, collected and recycled by an operation such as filtration of the reaction liquid.

The present invention has been made in view of the above-mentioned finding and solved the above-mentioned problem by providing a catalyst for alkylation, which comprises an inorganic structural material having an ion-exchange ability and a metal ion having a valency of 2 or more, the metal ion being supported on the inorganic structural material, and a process for producing an alkylaromatic hydrocarbon compound, including reacting an aromatic hydrocarbon compound and a compound having an unsaturated bond in the presence of the catalyst for alkylation.

Advantageous Effects of Invention

The catalyst for alkylation of the present invention has industrially suitable activity and selectivity and can be readily separated, collected and recycled.

Furthermore, according to the process for producing an alkylaromatic hydrocarbon compound of the present invention using the catalyst for alkylation of the present invention, an alkylaromatic hydrocarbon compound can be produced at a high yield and a high selectivity.

DESCRIPTION OF EMBODIMENTS

Although the inorganic structural material having an ion-exchange ability that constitutes the catalyst for alkylation of the present invention is not specifically limited as long as it is an inorganic structural material having an ion-exchange ability, it is preferably an inorganic structural material containing silicon and aluminum as main components. Examples of such inorganic structural material containing silicon and aluminum as main components may include silica-alumina, zeolite, mesoporous silica, hydroxyapatite, clays such as hydrotalcite, and the like, of which zeolite is specifically preferable.

The zeolite is not limited, and for example, either of a Y-type, an A-type, a ferrierite-type, ZSM-5 (an MFI-type), ZSM-12 (an MTW-type), a mordenite-type, a beta-type, an X-type, a T-type and the like can be used, and zeolites obtained by exchanging the cation ($H^+$, $NH_4^+$, metal ion and the like) in these zeolites, those obtained by changing the Si/Al ratio in the backbone, those obtained by replacing the Si in the backbone with other metal such as Ti, Sn and Zr, and the like can also be used. As these zeolites, commercial products can be used.

The Si/Al ratio of the zeolite is not limited and may be, for example, 0.01 to 100, preferably 1 or more, more preferably 2 or more, and preferably 80 or less, more preferably 60 or less.

The metal ion to be supported on the above-mentioned inorganic structural material may be an ion having a valency of 2 or more, and examples thereof may include lanthanoid metals (a collective term of the elements of atomic numbers 57 to 71), yttrium, magnesium, calcium, strontium, gallium, indium and the like which are polyvalent ions, of which lanthanide metals are preferable, and lanthanum, cerium, praseodymium, neodymium, samarium and ytterbium are specifically preferable. These may be ion species, or metal species formed by a reduction treatment or the like of ion species.

The supporting amount of the metal ion to be supported on the inorganic structural material is preferably in the range of 1 to 30% by mass, more preferably in the range of 3 to 20% by mass of the weight of the catalyst for alkylation. When the supporting amount of the metal ion is too small, sufficient activity may not be expressed, and when the supporting amount is too much, the yield and selectivity of the alkylaromatic hydrocarbon compound may be decreased.

By supporting the above-mentioned metal ion on the above-mentioned metal inorganic structural material, an acidic property (acid function) is expressed on the above-mentioned inorganic structural material. The acidic property refers to the characteristic of a Lewis acid of the ion itself and/or the characteristic of a Broensted acid by polarization of water which is/are expressed by ion-exchanging of $H^+$, $NH_4^+$ or a charge-compensating alkali metal ion with a metal ion having a valency of 2 or more so as to compensate the charge in the inorganic structural material having an ion-exchange ability.

As the process for supporting the metal ion on the inorganic structural material, a conventionally used process such as a process of evaporation to dryness, a pore-filling process and an ion-exchanging process can be used, and preferable processes are, but are not limited to, a pore-filling process and an ion-exchanging process from the viewpoint that the dispersibility of the metal ion to be supported on the inorganic structural material is improved.

It is preferable to remove moisture that is adsorbed by the above-mentioned inorganic structural material on which the metal ion is supported, from the viewpoint of expression of a catalyst activity. As a process for removing the adsorbed moisture, it is preferable to dry the inorganic structural material after supporting of the metal ion and bake the inorganic structural material at 400 to 600° C. for 1 to 12 hours, and it is specifically preferable to bake the inorganic structural material under an inert gas atmosphere such as nitrogen and argon.

In the case when the adsorbed moisture is not removed sufficiently, it is possible that the expression of the catalyst activity is decreased by the adsorbed moisture and the activity and selectivity are decreased.

The process for producing an alkylaromatic hydrocarbon compound of the present invention includes reacting an aromatic hydrocarbon compound and a compound having an unsaturated bond in the presence of the above-mentioned catalyst for alkylation.

The aromatic hydrocarbon compound that is alkylated in the present invention may be any one as long as it is a compound having at least one aromatic ring, and an aromatic hydrocarbon compound represented by general formula (1) below is specifically preferable.

[Chem. 1]

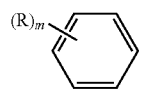

(1)

wherein R is a substituent, specifically a substituent having 1 to 5 carbon atoms (this may include an oxygen atom and a nitrogen atom), and m is an integer of 0 to 4.

Examples of the substituent represented by R in the above-mentioned general formula (1) may include an alkyl group having 1 to 5 carbon atoms, an alkoxy group having 1 to 5 carbon atoms, an alkoxycarbonyl group having 1 to 5 carbon atoms, an aryloxycarbonyl group, an alkanoyloxy group having 1 to 5 carbon atoms, an alkyl group having 1 to 5 carbon atoms in which the hydrogen of the alkyl group is substituted with an acetyl group or a halogen group, a nitro group and a halogen group, and the like, and a methyl group, an ethyl group, an n-propyl group, a methoxycarbonyl group, an ethoxycarbonyl group and an n-propoxycarbonyl group are specifically preferable.

Specific examples of the aromatic hydrocarbon compound represented by the above-mentioned general formula (1) may include toluene, ortho-xylene, meta-xylene, para-xylene, ethylbenzene, n-propylbenzene, isopropylbenzene, n-butylbenzene, t-butylbenzene, 1-ethyl-2-methyl-benzene, 1-ethyl-3-methyl-benzene, 1,2-diethylbenzene, phthalic acid, dimethyl phthalate, diethyl phthalate, dipropyl phthalate, 2-methylbenzoic acid, 2-methylbenzoic acid methyl ester and the like. Among these, aromatic hydrocarbon compounds wherein the substituent represented by R in the above-mentioned formula is a methyl group or an alkoxycarbonyl group are preferable in view of quickness of the reaction and easy availability of the raw materials, and toluene, ortho-xylene, meta-xylene and dimethyl phthalate are specifically preferable.

As the compound having an unsaturated bond used in the invention, a substituted alkene having a double bond is preferable, a cycloalkene is more preferable, and a cyclohexene compounds represented by the following general formula (2) is specifically preferable.

[Chem. 2]

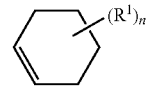

(2)

wherein $R^1$ is a substituent, specifically a substituent having 1 to 5 carbon atoms (this may include an oxygen atom and a nitrogen atom), and n is an integer of 0 to 4. $R^1$ is not bound to the carbon atom of the double bond of the cyclohexene. $R^1$ may be the same as or different from R in the general formula (1).

As the substituent represented by $R^1$ in the above-mentioned general formula (2), a substituent similar to the substituent represented by R in the general formula (1) can be exemplified, and specific examples may include an alkyl group having 1 to 5 carbon atoms, an alkoxy group having 1 to 5 carbon atoms, an alkoxycarbonyl group having 1 to 5 carbon atoms, an aryloxycarbonyl group, an alkanoyloxy group having 1 to 5 carbon atoms, an alkyl group having 1 to 5 carbon atoms in which the hydrogen of the alkyl group is substituted with an acetyl group or a halogen group, a nitro group and a halogen group, and the like, and a methyl group, an ethyl group, an n-propyl group, a methoxycarbonyl group, an ethoxycarbonyl group and an n-propoxylcarbonyl group are specifically preferable.

Specific examples of the cyclohexene compounds represented by the above-mentioned general formula (2) may include alkylcyclohexenes such as 4,5-dimethyl-1-cyclohexene, 3,4-dimethyl-1-cyclohexene, 3,5-dimethyl-1-cyclohexene, 3,6-dimethyl-1-cyclohexene, 3,4-diethyl-1-cyclohexene, 4,5-diethyl-1-cyclohexene, 3,4-di-n-propyl-1-cyclohexene, 4,5-di-n-propyl-1-cyclohexene, 3,4-diisopropyl-1-cyclohexene, 4,5-diisopropyl-1-cyclohexene, 3,4-di-n-butyl-1-cyclohexene, 4,5-di-n-butyl-1-cyclohexene, 3,4-di-t-butyl-1-cyclohexene, 4,5-di-t-butyl-1-cyclohexene, 4-ethyl-5-methyl-1-cyclohexene, 3-ethyl-5-methyl-1-cyclohexene, 3-methyl-1-cyclohexene, 4-methyl-1-cyclohexene, 3-ethyl-1-cyclohexene, 4-ethyl-1-cyclohexene, 3,4-dimethyl-1-cyclopentene and 3,5-dimethyl-1-cyclopentene, cyclohexenedicarboxylic acid esters such as 1-cyclohexene-4,5-dicarboxylic acid esters, 3,4-dimethyl-1-cyclopentene, 3,5-dimethyl-1-cyclopentene and the like, of which 3,4-dimethyl-1-cyclohexene, 4,5-dimethyl-1-cyclohexene, 3,6-dimethyl-1-cyclohexene and 1-cyclohexene-4,5-dicarboxylic acid esters are specifically preferable. In the compounds in which two or more substituents of the cycloalkene are present, the steric configuration thereof may be a cis- or trans- steric configuration.

The cyclohexene compounds represented by the above-mentioned general formula (2) can be produced by a known method such as a Diels-Alder reaction of a diene compound and an allyl compound, dehydration of an alkylcyclohexanol, and dehydrohalogenation of a halogenated cyclohexane.

Alternatively, it can also be produced by catalytic partial hydrogenation of a corresponding aromatic hydrocarbon. Examples of the aromatic hydrocarbon may include toluene, ortho-xylene, meta-xylene, para-xylene, ethylbenzene, n-propylbenzene, isopropylbenzene, n-butylbenzene, t-butylbenzene, 1,2-methylethylbenzene, 1,3-methylethylbenzene, 1,2-diethylbenzene, phthalic acid, dimethyl phthalate, diethyl phthalate, dipropyl phthalate, 2-methylbenzoic acid, 2-methylbenzoic acid methyl ester and the like. Among these, aromatic hydrocarbons wherein the substituent on the aromatic ring is a methyl group or an alkoxycarbonyl group are preferable in view of quickness of the reaction and easy availability of the raw materials, and toluene, ortho-xylene, meta-xylene and dimethyl phthalate are specifically preferable.

As the catalyst used for the catalytic partial hydrogenation of the above-mentioned aromatic hydrocarbon that is used for the production of the cyclohexene compounds represented by the above-mentioned general formula (2), a catalyst that is used in general hydrogenation can be used. Specific examples may include metals such as ruthenium, rhodium, rhenium, platinum, palladium, nickel, cobalt, chromium, iridium and copper. These metals can be used after supporting on a support such as active carbon, alumina, silica, zirconia, titania and magnesia, or can be directly used as metal microparticles.

In the process for producing an alkylaromatic hydrocarbon compound of the present invention, the ratio of use of the aromatic hydrocarbon compound to the compound having an unsaturated bond is such a ratio that the molar ratio of the compound having an unsaturated bond to the aromatic hydrocarbon compound becomes preferably 0.001 to 1000, more preferably 0.01 to 100. When the compound having an unsaturated bond is too low, a sufficient reaction velocity cannot be obtained, whereas when the compound having an unsaturated bond is too much, it is not cost efficient.

The amount of the above-mentioned catalyst for alkylation is preferably 0.01 to 200% by mass, more preferably 0.1 to 100% by mass with respect to the mass of the compound having an unsaturated bond. When the amount of the catalyst for alkylation is too low, a sufficient reaction velocity cannot be obtained, whereas when the catalyst is too much, it is not cost efficient.

The reaction of the aromatic hydrocarbon compound and the compound having an unsaturated bond (alkylation) may be performed in a solvent, or may be performed without a solvent. As the solvent used for the alkylation, a compound that is inert to the alkylation is used, and nitromethane, nitrobenzene, carbon disulfide and acetonitrile which are widely used in alkylation, as well as aliphatic hydrocarbons such as hexane, cyclohexane, petroleum ether, octane and decaline can be used. Alternatively, the aromatic hydrocarbon compound can be used also as a solvent. Alternatively, an alkylcyclohexane that is by-produced in the above-mentioned production of the alkylcyclohexane can also be used.

In the case when the aromatic hydrocarbon compound or compound having an unsaturated bond has an ester substituent, it is preferable to add an alcohol, preferably methanol, ethanol or propanol, in a small amount (1 mol to 10 mol with respect to 1 mol of the ester substituent) so as to suppress hydrolysis by the catalyst.

The pressure during the alkylation is in the range of 0.1 to 30 MPa, preferably 0.1 to 15 MPa in total pressure. The reaction is preferably conducted under a nitrogen gas atmosphere, and the nitrogen gas may be diluted with a gas that does not affect the reaction such as argon and carbon dioxide.

The reaction temperature is in the range of 20 to 300° C., preferably 80 to 250° C. The reaction time varies depending on the reaction condition, and is generally several minutes to several hours.

A preferable scheme of the alkylation in the present invention is reacting the aromatic hydrocarbon compound and cyclohexene compounds in the presence of the catalyst to give a cyclohexyl aromatic hydrocarbon compound, as shown in formula below.

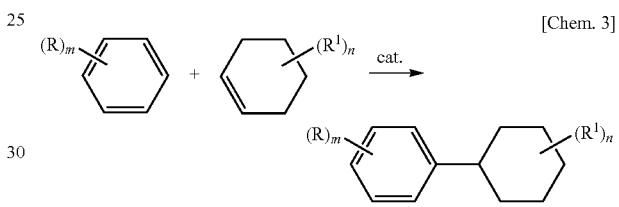

[Chem. 3]

Furthermore, a more preferable scheme of the alkylation of the present invention is reacting the aromatic hydrocarbon compound and cyclohexenedicarboxylic acid ester in the presence of the catalyst to give a dialkoxycarbonylcyclohexylbenzene compound, as shown in formula below.

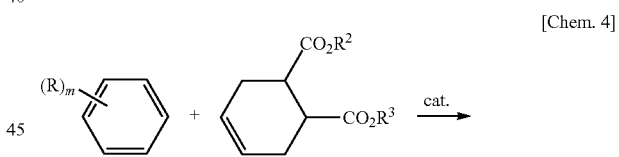

[Chem. 4]

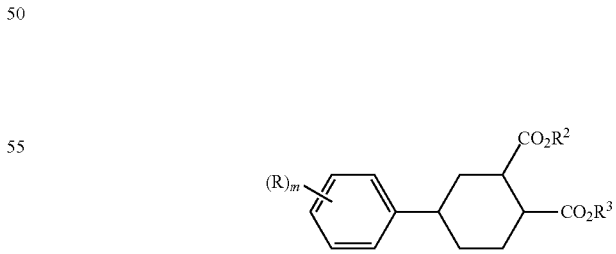

wherein $R^2$ and $R^3$ may be the same or different and each represents an alkyl group having 1 to 5 carbon atoms.

Among the alkylaromatic hydrocarbon compounds obtained by the production process of the present invention, for example, a 3,4-dialkoxycarbonylcyclohexyl-3',4'-dimethylbenzene represented by formula (3) below is a novel compound.

[Chem. 5]

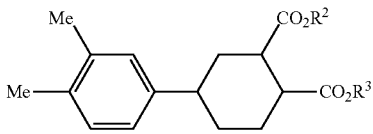

(3)

The catalyst for alkylation after the reaction can be readily separated and collected by an operation of separation by filtration to separate a solid and a liquid, and the collected catalyst for alkylation can be recycled.

Among the alkylaromatic hydrocarbon compounds obtained by the production process of the present invention, for example, in alkylcyclohexyl(alkyl)benzenes, the cyclohexane ring can be treated with a catalyst having a dehydrogenation ability. Specific examples of the catalyst may include metals such as ruthenium, rhodium, rhenium, platinum, palladium, nickel, cobalt, chromium, iridium and copper. These metals can be used after supporting on a support such as active carbon, alumina, silica, zirconia, titania and magnesia, or can be directly used as metal microparticles. When dehydrogenation is conducted in the presence of such catalyst, an alkylbiphenyl can be produced.

The alkylbiphenyl as obtained can be separated by a conventional method (for example, distillation, crystallization, column separation and the like), and if conventionally known reactions are applied by using this alkylbiphenyl, corresponding biphenyl dicarboxylic acid, biphenyl tetracarboxylic acid and biphenyl tetracarboxylic acid anhydride can be produced. These compounds are useful as polymer raw materials for polyimides, polyamideimides and the like, and as curing agents for epoxy resins.

EXAMPLES

Hereinafter the present invention will further be explained in detail by Examples, but the present invention is not limited at all by these Examples.

The yields and selectivities described in Examples and Comparative Examples below are based on the compound having an unsaturated bond, and were calculated by the following formula:

Yield (%)=(mmol of the alkylated product)/(mmol of the compound having an unsaturated bond as used)×100

Selectivity (%)=(mmol of the alkylated product)/(mmol of the compound having an unsaturated bond as reacted)×100

Example 1

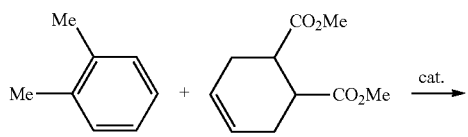

[Chem. 6]

-continued

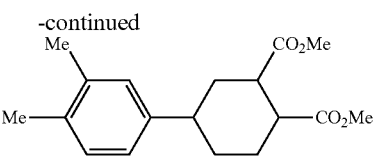

A liquid obtained by dissolving 2 g of lanthanum nitrate hexahydrate in 100 ml of ion-exchanged water was added dropwise at a room temperature to a suspension liquid obtained by adding 200 ml of ion-exchanged water to 5 g of H-type Y-zeolite supplied by Tosoh Corporation (HSZ-320HOA) (Si/Al ratio=2.8), and then heated at 90° C. for 3 hours. The solid was separated therefrom by a centrifugal machine, washed with 45 ml of ion-exchanged water five times, and dried at 85° C. overnight. This was calcined at 500° C. for 2 hours under an air atmosphere to give a catalyst for alkylation of the present invention (hereinafter abbreviated as La/HY). The amount of La in the solid was measured by ICP (Inductively Coupled Plasma) and found to be 5.6% by mass.

Alkylation was performed as follows by using an autoclave made of SUS equipped with a 50 ml glass insert tube. To the glass insert tube were added 0.10 g of the above-mentioned La/HY as a catalyst for alkylation (100% by mass with respect to the used amount of the compound having an unsaturated bond), 0.16 g of tridecane (an internal standard), 0.1 g (0.53 mmol) of 1-cyclohexene-4,5-dicarboxylic acid methyl ester (hereinafter abbreviated as CEDA) as the compound having an unsaturated bond, and 3 g (28.30 mmol) of ortho-xylene as the aromatic hydrocarbon compound. The system was purged with nitrogen gas three times and sealed under a nitrogen atmosphere. This autoclave was immersed in an oil bath that had been set to 180° C. in advance to initiate a reaction. At after 2 hours, the reactor was cooled by water, and the gas was released from the reactor. In the reaction liquid, 3,4-dimethoxycarbonylcyclohexyl-3',4'-dimethylbenzene (hereinafter abbreviated as CDMB) that is an alkylated product as produced, 1-cyclohexene-4,5-dicarboxylic acid anhydride and the like were quantified by an internal standard process using gas chromatography by an FID detector. As the result thereof, CDMB was generated with a yield of 49.6% and a selectivity of 51.0%.

CDMB is a novel compound represented by the following physical properties.

Boiling point: 166° C./66 Pa $^1$H NMR (500 MHz, CDCl$_3$): δ 1.44-1.48 (m, 1H), 1.69-1.76 (m, 1H), 1.95-2.04 (m, 2H), 2.13-2.16 (m, 1H), 2.22 (s, 3H), 2.24 (s, 3H), 2.33-2.38 (m, 1H), 2.48-2.56 (m, 2H), 3.37-3.96 (m, 1H), 3.71 (s, 3H×2) 6.92 (d, J=7.7 Hz, 1H), 6.96 (s, 1H), 7.06 (d, J=7.7 Hz, 1H)

$^{13}$C NMR (500 MHz, CDCl$_3$): δ 19.3, 19.8, 24.5, 33.2, 35.5, 39.0, 42.0, 43.3, 51.8, 123.9, 128.2, 129.7, 134.4, 136.5, 143.4, 173.8, 174.2.

IR (neat, cm$^{-1}$): 3450, 3000, 2950, 2860, 1734.

Elemental analysis: C$_{18}$H$_{24}$O$_4$: Measured value C, 70.72; H, 7.78. Calculated value C, 71.03; H, 7.95.

Comparative Example 1

Alkylation was conducted in a similar manner to that in Example 1, except that La/HY as a catalyst for alkylation was not used. As the result thereof, generation of CDMB cannot be detected by GLC.

Comparative Example 2

Alkylation was conducted in a similar manner to that in Example 1, except that H-type Y-zeolite supplied by Tosoh Corporation (HSZ-320HOA) (hereinafter abbreviated as HY (Si/Al=2.8)) was used instead of La/HY as a catalyst for alkylation, and that CEDA was used in the amount shown in Table 1. As the result thereof, CDMB was generated with a yield of 7.0% and a selectivity of 17.5%.

Example 2

A catalyst for alkylation of the present invention (hereinafter abbreviated as Y/HY) was obtained in a similar manner to that in Example 1, except that yttrium nitrate hexahydrate was used instead of lanthanum nitrate hexahydrate. The amount of Y in the solid was measured by ICP and found to be 4.6% by mass.

Alkylation was conducted in a similar manner to that in Example 1, except that the above-mentioned Y/HY was used as a catalyst for alkylation instead of La/HY and that CEDA was used in the amount shown in Table 1. As the result thereof, CDMB was generated with a yield of 19.9% and a selectivity of 31.6%.

Example 3

A catalyst for alkylation of the present invention (hereinafter abbreviated as Sm/HY) was obtained in a similar manner to that in Example 1, except that samarium nitrate hexahydrate was used instead of lanthanum nitrate hexahydrate. The amount of Sm in the solid was measured by ICP and found to be 5.5% by mass.

Alkylation was conducted in a similar manner to that in Example 1, except that the above-mentioned Sm/HY was used as a catalyst for alkylation instead of La/HY and that CEDA was used in the amount shown in Table 1. As the result thereof, CDMB was generated with a yield of 45.1% and a selectivity of 47.9%.

Example 4

A catalyst for alkylation of the present invention (hereinafter abbreviated as La/USY (Si/Al=6)) was obtained in a similar manner to that in Example 1, except that USY zeolite supplied by NE Chemcat Corporation (Si/Al ratio=6) was used instead of H-type Y-zeolite supplied by Tosoh Corporation (HSZ-320HOA). The amount of La in the solid was measured by ICP and found to be 1.9% by mass.

Alkylation was conducted in a similar manner to that in Example 1, except that the above-mentioned La/USY (Si/Al=6) was used as a catalyst for alkylation instead of La/HY and that CEDA was used in the amount shown in Table 1. As the result thereof, CDMB was produced with a yield of 35.2% and a selectivity of 36.7%.

Example 5

A catalyst for alkylation of the present invention (hereinafter abbreviated as La/USY (Si/Al=30)) was obtained in a similar manner to that in Example 1, except that USY zeolite manufactured by NE Chemcat Corporation (Si/Al ratio=30) was used instead of H-type Y-zeolite manufactured by Tosoh Corporation (HSZ-320HOA). The amount of La in the solid was measured by ICP and found to be 0.9% by mass.

Alkylation was conducted in a similar manner to that in Example 1, except that the above-mentioned La/USY (Si/Al=30) was used as a catalyst for alkylation instead of La/HY and that CEDA was used in the amount shown in Table 1. As the result thereof, CDMB was produced with a yield of 36.5% and a selectivity of 38.1%.

The catalysts for alkylation used in Examples 1 to 5 and Comparative Examples 1 to 2, the use amounts of CEDA, and the yield and selectivity of CDMB (alkylated product) are summarized in Table 1.

TABLE 1

Results of alkylation (180° C. × 2 hr)

| | Catalyst for alkylation | Use amount of CEDA (mmol) | Yield of CDMB (%) | CDMB selectivity (%) |
|---|---|---|---|---|
| Example 1 | La/HY(Si/Al = 2.8) | 0.53 | 49.6 | 51.0 |
| Comparative Example 1 | Not used | 0.53 | 0 | 0 |
| Comparative Example 2 | HY(Si/Al = 2.8) | 0.58 | 7.0 | 17.5 |
| Example 2 | Y/HY(Si/Al = 2.8) | 0.55 | 19.9 | 31.6 |
| Example 3 | Sm/HY(Si/Al = 2.8) | 0.53 | 45.1 | 47.9 |
| Example 4 | La/USY(Si/Al = 6) | 0.54 | 35.2 | 36.7 |
| Example 5 | La/USY(Si/Al = 30) | 0.52 | 36.5 | 38.1 |

Example 6

Alkylation was conducted in a similar manner to that in Example 1, except that 6 mmol of methanol was further added to the glass insert tube. As the result thereof, CDMB was produced with a yield of 71.5% and a selectivity of 92.6%.

Example 7

Alkylation was conducted in a similar manner to that in Example 3, except that 6 mmol of methanol was further added to the glass insert tube. As the result thereof, CDMB was produced with a yield of 73.3% and a selectivity of 74.8%.

Example 8

Alkylation was conducted in a similar manner to that in Example 4, except that 6 mmol of methanol was further added to the glass insert tube and CEDA was used in the amount shown in Table 2. As the result thereof, CDMB was produced with a yield of 56.9% and a selectivity of 77.1%.

Example 9

Alkylation was conducted in a similar manner to that in Example 5, except that 6 mmol of methanol was further added to the glass insert tube and CEDA was used in the amount shown in Table 2. As the result thereof, CDMB was produced with a yield of 92.2% and a selectivity of 94.4%.

The catalysts for alkylation used in Examples 6 to 9, the use amounts of CEDA, and the yield and selectivity of CDMB (alkylated product) are summarized in Table 2.

TABLE 2

Results of alkylation (methanol was added)

| | Catalyst for alkylation | Use amount of CEDA (mmol) | Yield of CDMB (%) | CDMB selectivity (%) |
|---|---|---|---|---|
| Example 6 | La/HY(Si/Al = 2.8) | 0.53 | 71.5 | 92.6 |
| Example 7 | Sm/HY(Si/Al = 2.8) | 0.54 | 73.3 | 74.8 |
| Example 8 | La/USY(Si/Al = 6) | 0.56 | 56.9 | 77.1 |
| Example 9 | La/USY(Si/Al = 30) | 0.54 | 92.2 | 94.4 |

Example 10

Alkylation was conducted in a similar manner to that in Example 9, except that the use amount of the catalyst for alkylation was 50% by mass with respect to the weight of the alkylation agent and that CEDA was used in the amount shown in Table 3. As the result thereof, CDMB was produced with a yield of 51.2% and a selectivity of 89.5%.

Example 11

Alkylation was conducted in a similar manner to that in Example 9, except that the use amount of the catalyst for alkylation was 10% by mass with respect to the weight of the compound having an unsaturated bond and that CEDA was used in the amount shown in Table 3. As the result thereof, CDMB was produced with a yield of 19.8% and a selectivity of 84.9%.

The use amounts (the amounts of the catalyst with respect to the mass of the compound having an unsaturated bond) of the catalysts for alkylation used in Examples 10 and 11, the use amounts of CEDA, and the yields and selectivity of CDMB (alkylated product) are summarized in Table 3.

TABLE 3

Change in amount of catalyst

| | Amount of catalyst with respect to weight of compound having unsaturated bond (mass %) | Use amount of CEDA (mmol) | Yield of CDMB (%) | CDMB selectivity (%) |
|---|---|---|---|---|
| Example 10 | 50 | 0.53 | 51.2 | 89.5 |
| Example 11 | 10 | 0.53 | 19.8 | 84.9 |

Example 12

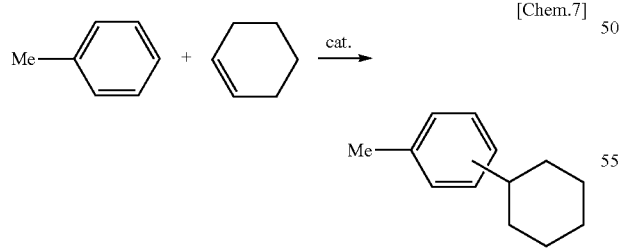
[Chem.7]

Alkylation was conducted in a similar manner to that in Example 1, except that 0.1 g (about 1.2 mmol) of cyclohexene as the compound having an unsaturated bond, 3 g (32.6 mmol) of toluene as the aromatic hydrocarbon compound, and 100% by mass of the LaHY catalyst with respect to the cyclohexene were charged, and that a reaction was performed at 180° C. for 2 hours.

After the reaction, the catalyst was separated by filtration by Chromatodisc and analyzed by GC. Cyclohexyl-methyl-benzene with plural isomers was obtained.

Example 13

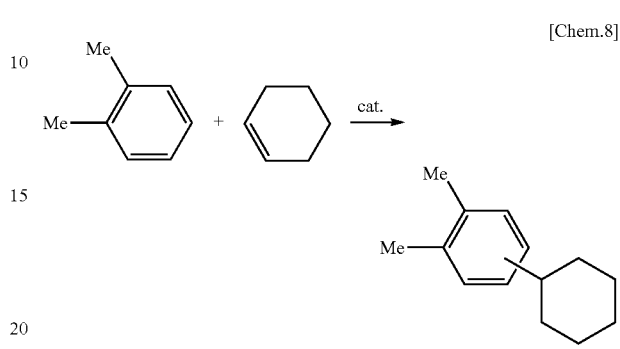
[Chem.8]

Alkylation was conducted in a similar manner to that in Example 1, except that 0.1 g (about 1.2 mmol) of cyclohexene as the compound having an unsaturated bond, 3 g (28.3 mmol) of o-xylene as the aromatic hydrocarbon compound, and 100% by mass of the LaHY catalyst with respect to the cyclohexene were charged, and that a reaction was performed at 180° C. for 2 hours.

After the reaction, the catalyst was separated by filtration by Chromatodisc and analyzed by GC. Cyclohexyl-dimethyl-benzene with plural isomers was obtained.

The raw materials and use amounts thereof, and the results of reaction (cyclohexene conversions and selectivities of the alkylated products) in Examples 12 and 13 are summarized in Table 4.

TABLE 4

| | Aromatic hydrocarbon compound (g) | Use amount of compound having unsaturated bond (cyclohexene) (mmol) | Conversion of cyclohexene (%) | Selectivity of alkylated product (%) |
|---|---|---|---|---|
| Example 12 | Toluene(3) | 1.25 | 100 | 97.6 |
| Example 13 | Ortho-xylene(3) | 1.30 | 100 | 97.7 |

The invention claimed is:

1. A process for producing an alkylaromatic hydrocarbon compound, comprising reacting an aromatic hydrocarbon compound represented by general formula (1),

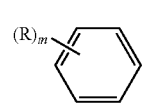
(1)

wherein R is a substituent, and m is an integer of 0 to 4, and a cyclohexenedicarboxylic acid ester in the presence of a catalyst for alkylation, wherein the catalyst for alkylation comprises an inorganic structural material having an ion-exchange ability and a metal ion having a valency of 2 or more, the metal ion being supported on the inorganic structural material, wherein the inorganic structural material having an ion-exchanging ability is a zeolite comprising silicon and aluminum as main components, and the metal ion is a lanthanide metal or yttrium.

2. The process for producing an alkylaromatic hydrocarbon compound according to claim 1, wherein the catalyst for alkylation is separated, collected and recycled after completion of the reaction.

3. A 3,4-dialkoxycarbonylcyclohexyl-3',4'-dimethylbenzene represented by formula (3) below:

[Chem. 3]

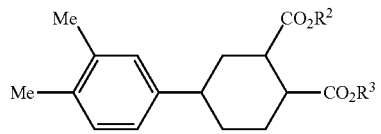

(3)

wherein $R^2$ and $R^3$ may be the same or different and each represents an alkyl group having 1 to 5 carbon atoms.

* * * * *